United States Patent [19]

Baker et al.

[11] Patent Number: 5,733,437
[45] Date of Patent: *Mar. 31, 1998

[54] METHOD FOR DETECTING SMALL MOLECULES IN AQUEOUS LIQUIDS

[76] Inventors: Mark D. Baker, 78 Laurelcrest Street, Bramalea Ontario, Canada, L6S 5W3; Chandana Senaratne, P O Box 1868, Kfupm, Dhahram, Saudi Arabia, 31261

[*] Notice: The term of this patent shall not extend beyond the expiration date of Pat. No. 5,730,857.

[21] Appl. No.: 665,609

[22] Filed: Jun. 18, 1996

Related U.S. Application Data

[63] Continuation-in-part of Ser. No. 255,734, Jun. 7, 1994, which is a continuation of Ser. No. 235,212, Apr. 29, 1994, abandoned, which is a division of Ser. No. 833,710, Feb. 11, 1992, abandoned.

[30] Foreign Application Priority Data

Feb. 13, 1991 [GB] United Kingdom .......... 9103053

[51] Int. Cl.$^6$ ...................................... G01N 27/26
[52] U.S. Cl. .................. 205/775; 204/400; 204/409; 205/780.5; 205/787; 205/789
[58] Field of Search ................... 204/400, 409; 205/775, 780.5, 781.5, 787, 788, 789

[56] References Cited

U.S. PATENT DOCUMENTS

| | | | |
|---|---|---|---|
| 2,614,976 | 10/1952 | Patnode et al. | 204/419 |
| 3,839,162 | 10/1974 | Ammer | 204/409 |
| 3,856,633 | 12/1974 | Fletcher | 204/419 |
| 3,865,708 | 2/1975 | Light et al. | 204/419 |
| 4,422,917 | 12/1983 | Hayfield | 204/290 F |
| 4,440,602 | 4/1984 | Dobson | 204/419 |
| 4,944,273 | 7/1990 | Baresel et al. | 204/424 |

OTHER PUBLICATIONS

Talanta, 1991, month unavailable vol. 39, No. 1, pp. 27–35, Analytical Implications of Zeolites in Overlayers at Electrodes, Debra R. Rolison, Robert J. Nowak, Timothy A. Welsh and Catherine G. Murray.

Anal. Chem., 1985, month unavailable, vol. 57, pp. 2379–2740 Voltammetric Determination of Nonelectroactive Ions at a Modified Electrode, James A. Cox, Basudev K. Das.

Anal. Chem., Dec. 1, 1989, vol. 61, No. 23, pp. 2594–2598, Amperometric Detection of Nonelectroactive Cations in Flow Systems at a Cupric Hexacyanoferrate Electrode, Karsten N. Thomsen, Richard P. Baldwin.

Analytica Chimica Acta, 1988, vol. 207, pp. 95–102, Accumulation and Voltammetric Measurement of Silver at Zeolite–Containing Carbon–Paste Electrodes, Joseph Wang, Teddy Martinez.

Abstract L1 Answer 5 of 36, AU: Nagai, Masayuki; Hibino, Masayuki, Nishino, Tadashi, Humidity Sensor Characteristics of Porous Zeolite Ceramics at Elevated Temperatures. Abstract L1 Answer 9 of 36, Chemical Sensor.
Abstract L1 Answer 14 of 36, AU: Uchikawa, Hidefusa, Manufacture of Moisture Sensitive Materials.
Abstract L1 Answer 19 of 36, Zeolite Humidity Sensors.
Abstract L1 Answer 28 of 36, Moisture Sensor.
Abstract L1 Answer 29 of 35, Moisture Sensor.

*Primary Examiner*—T. Tung
*Attorney, Agent, or Firm*—Lynn C. Schumacher; Dowell & Dowell

[57] ABSTRACT

A method for detecting organic molecules such as benzene, xylene, ethylbenzene and toluene present in trace quantities in aqueous solutions is provided. The method uses a zeolite having a multiple cage structure, specifically cages of two different volumes. The zeolite is chosen so that the organic molecules are able to access the zeolite on the basis of size. The small cages contain electroactive ions therein and the larger cages contain electroinactive counter cations therein. An aqueous liquid sample to be tested for small molecules is flowed into contact with the zeolite whereby at least some of the electroactive ions in the small cages are released into the aqueous liquid sample by small molecules entering the larger cages and coupling with the electroactive ions in the smaller cages and exiting the zeolite. Thereafter the liquid sample is flowed into contact with an electrode downstream of the zeolite and a potential is applied to the electrode with respect to a counter-electrode effective to cause an electrochemical reaction of the electroactive ions.

11 Claims, 9 Drawing Sheets

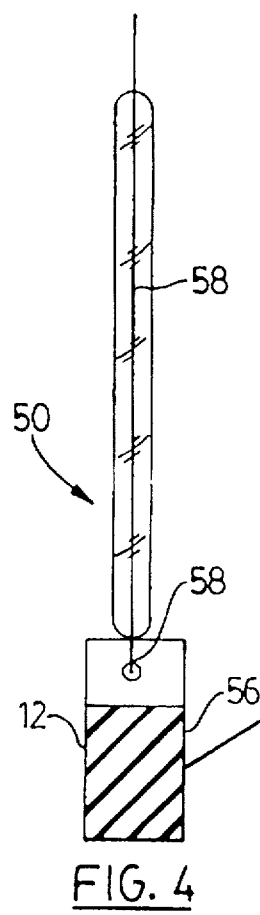
FIG. 4
FIG. 4A
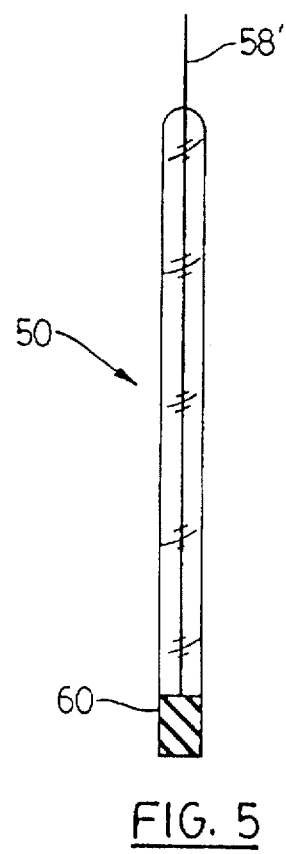
FIG. 5
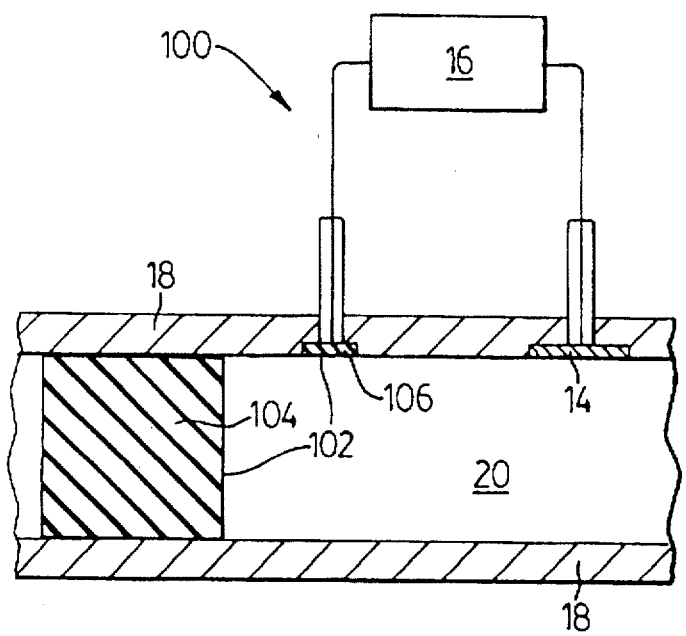
FIG. 9

METHOD FOR DETECTING SMALL MOLECULES IN AQUEOUS LIQUIDS

The present invention is a continuation-in-part application of U.S. patent application Ser. No. 08/255,734 filed on Jun. 7, 1994 entitled "METHOD FOR DETECTING IONS AND SMALL MOLECULES IN AQUEOUS AND NON-AQUEOUS LIQUIDS", which was a continuation of U.S. patent application Ser. No. 08/235,212 filed on Apr. 29, 1994, now abandoned, which was a divisional application of U.S. patent application Ser. No. 07/833,710 filed on Feb. 11, 1992, now abandoned, entitled "SOLUTION PHASE ION AND WATER SENSITIVE DETECTOR".

FIELD OF THE INVENTION

The present invention relates generally to a method and apparatus for detecting ions and small molecules in aqueous and non-aqueous liquids. More particularly the invention is directed to a method of detecting organic molecules in liquids.

BACKGROUND OF THE INVENTION

Solution phase ion detectors form an integral part of certain analytical procedures, one important application being ion chromatography. Indeed, as an analytical technique ion chromatography did not really make an impact until relatively recently (1975) when a viable solution phase ion detector was developed. This ion chromatograph, marketed by Dionex Corporation, uses a conductometric based universal ion detector. Since conductivity is a bulk property measurement, it is by itself not capable of good sensitivity since the mobile phases used in ion chromatography are highly conducting and the conductivity of the species being detected is a small fraction of the overall solution conductivity thereby giving rise to a significant dynamic range problem.

One method of overcoming this problem is to employ a chemical suppression technique wherein the eluent conductivity is decreased while the analyte conductivity is increased thereby increasing the signal contrast above the background. While chemical suppression techniques give a superior detection limit (roughly an order of magnitude), the technique is not applicable to many materials including heavy metals and organics to mention a few.

Other detection techniques such as direct electrochemical detection cannot be universally applied as an aqueous ion detector since the reduction potentials of many cations and molecules lie outside the electrochemical stability region of water.

The specific sensing of water in organic solvents is deemed important in the monitoring of industrial feedstocks. In this area, interference (i.e. non-selective responses) has been a severe problem. In addition, the detection of water in organic solvents is deemed important in chemical laboratories. Karl Fisher titration systems are currently available for this application and have detection limits in the vicinity of about 1 ppm. In addition, the specific sensing of organic molecules in aqueous liquids, for example, but not limited to BTEX (benzene, toluene, ethylbenzene and xylene), below 1 ppm is also important in for example environmental analysis.

SUMMARY OF THE INVENTION

The method and detector of the present invention utilizes an electrochemical detection technique, whereby both organic and inorganic species may be detected. The detector is not limited in scope by the reduction or oxidation potentials of these species in contrast to the detectors previously used.

In one aspect of the invention there is provided a method for detecting small molecules such as benzene, toluene, ethylbenzene or xylene in aqueous liquid samples. The method comprises the steps of providing a zeolite having a plurality of first cages and a plurality of second cages which are larger than the first cages. The zeolite is chosen on the basis that the organic molecules being detected for are able to access said zeolite on the basis of size. The first cages contain electroactive ions therein and the second cages contain therein electroinactive counter cations. An aqueous liquid sample to be tested for small molecules is provided and contacted to the zeolite. When small molecules are present at least some of the electroactive ions in the first cages are released into the liquid sample by small molecules entering the second cages and coupling with the electroactive ions in the first cages and exiting the zeolite into the liquid sample. The method includes bringing the liquid sample containing the electroactive ions into contact with an electrode after the liquid sample has contacted the zeolite and applying a potential to the electrode with respect to a counter-electrode effective to cause an electrochemical reaction of the electroactive ions.

In this aspect of the invention the zeolite is preferably zeolite Y, the electroactive ions are silver and the electroinactive counter cation is $NH_4^+$.

In another aspect of the invention there is provided a method for detecting small molecules such as benzene, toluene, ethylbenzene or xylene in aqueous liquid samples. The method comprises the steps of providing a zeolite having first cages and second cages with the second cages having a larger volume than the first cages. The zeolite is chosen on the basis that the organic molecules are able to access the zeolite on the basis of size. The first cages contain electroactive ions therein and the second cages contain electroinactive counter cations therein. The method comprises flowing an aqueous liquid sample to be tested for small molecules into contact with the zeolite whereby at least some of the electroactive ions in the first cages are released into the aqueous liquid sample by small molecules entering the second cages and coupling with the electroactive ions in the first cages and exiting the zeolite. Thereafter the liquid sample is flowed into contact with an electrode downstream of the zeolite and a potential is applied to the electrode with respect to a counter-electrode effective to cause an electrochemical reaction of the electroactive ions.

BRIEF DESCRIPTION OF THE DRAWINGS

The method and apparatus of the present invention will now be described, by way of example only, with respect to the following drawings, in which:

FIG. 4 is an elevational view of a zeolite/carbon/polystyrene composite detector electrode showing detail of the composite electrode;

FIG. 4A is an enlargement of a portion of the electrode of FIG. 4;

FIG. 5 is an elevational view of a zeolite/epoxy bonded graphite composite detector electrode;

FIG. 9 is a diagrammatic view of an alternative embodiment of the detector electrode;

DETAILED DESCRIPTION OF THE INVENTION

Figure 1:
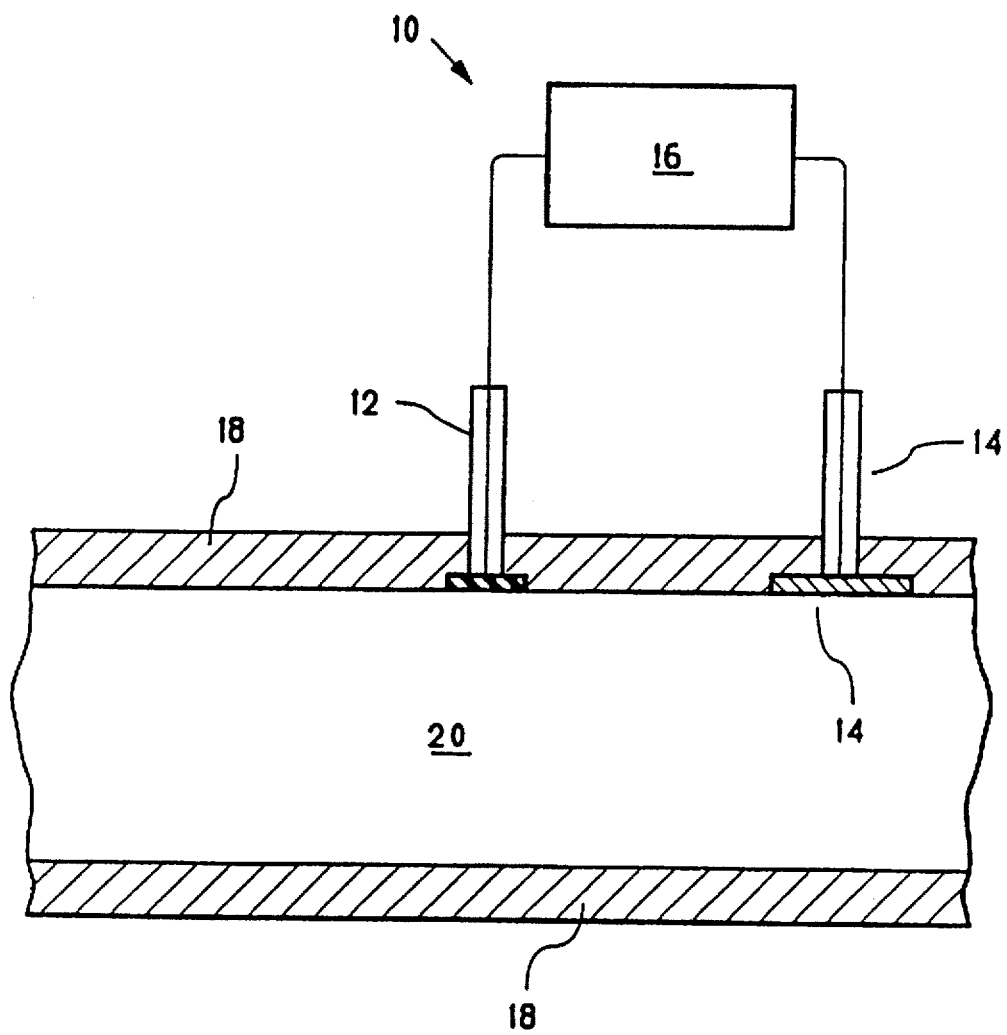
FIG. 1 is a diagrammatic view of a detector embodying the subject invention.

Referring first to FIG. 1, an ion and small molecule detector 10 comprises a zeolite based detector electrode 12 and a suitable counter electrode 14 both electrically coupled to a potentiostat 16. Electrodes 12 and 14 are shown mounted in the side wall of a liquid flow (or static) system 18. Solution 20 is the solution being tested and may be an aqueous or non-aqueous medium. Although this embodiment of the detector shows a two electrode configuration, it will be appreciated by those skilled in the art that three electrode configurations employing a reference electrode are routinely employed for providing potential control of the detector electrode.

Figure 2:
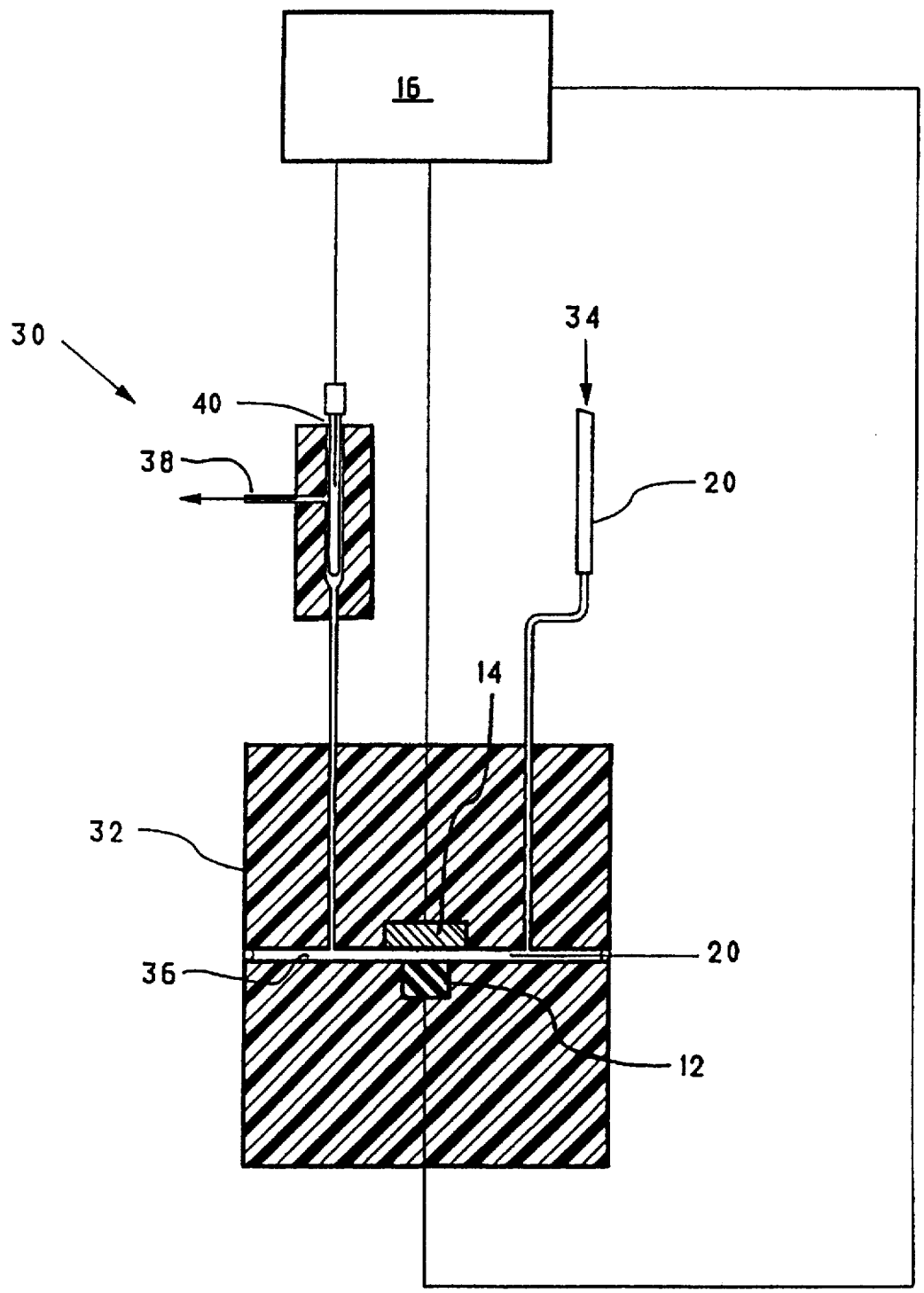
FIG. 2 is a diagrammatic view of an alternative embodiment of the detector.

FIG. 2 illustrates an alternative view of a detector 30 of the present invention. Detector 30 comprises zeolite based detector electrode 12 but now adapted to be inserted into a commercially available electrochemical detector housing 32 utilized in liquid chromatography. A solution inlet 34 admits solution 20 into a channel 36 containing detector electrode 12 and counter electrode 14 in an adjacently spaced relation. Solution 20 is flowed between electrodes 12 and 14 to exit detector 30 at an exit port 38. Detector 30 is provided with a reference electrode 40 located adjacent exit port 38. Detector electrode 12, counter electrode 14 and reference electrode 40 are electrically coupled to potentiostat 16.

Figure 3:
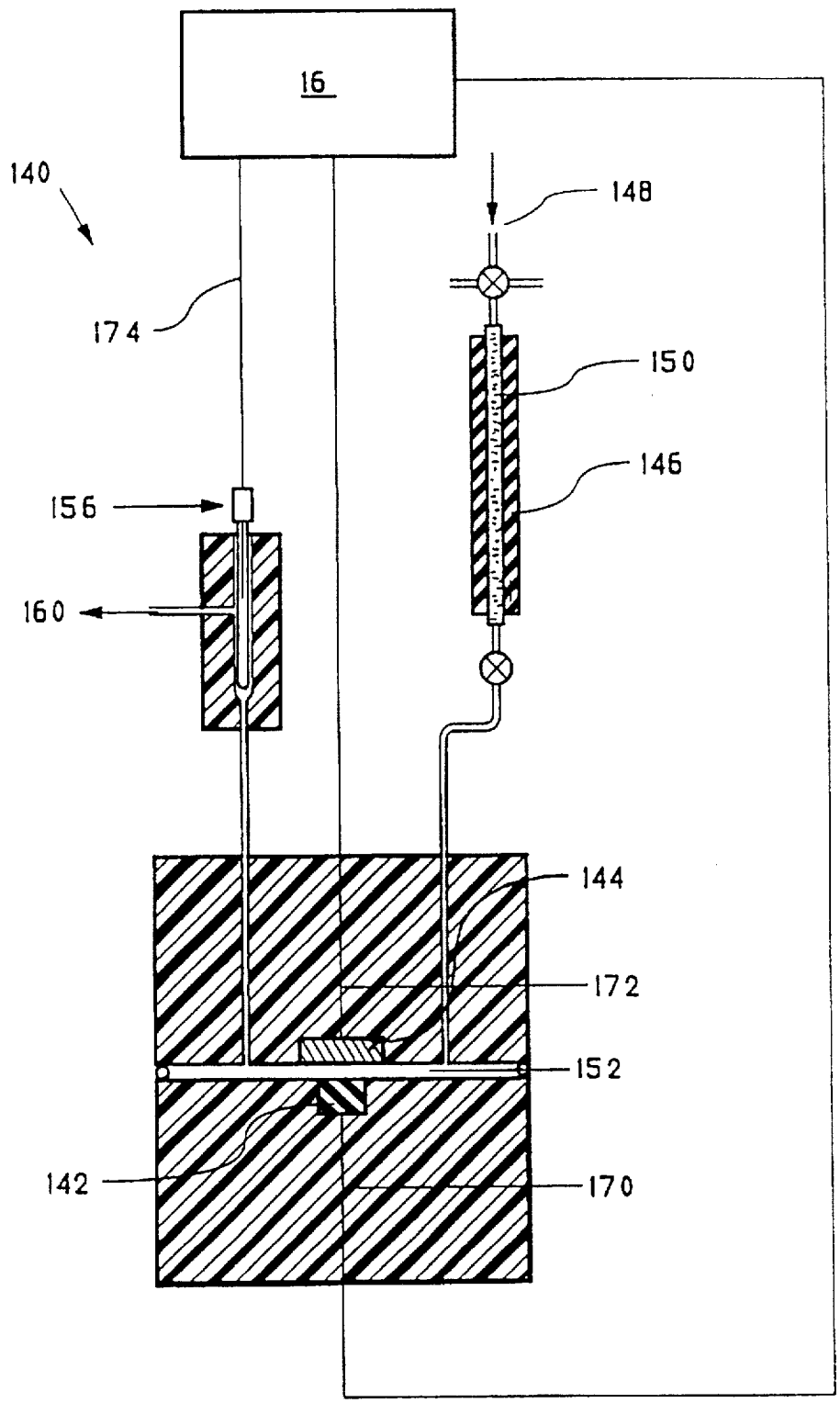
FIG. 3 is a diagrammatic view of yet another embodiment of the detector.

Referring to FIG. 3, another embodiment of a detector is shown generally at 140 and includes a conducting detector electrode 142, a counter electrode 144 plus a zeolite column 146. A solution inlet 148 admits solution 150 into zeolite column 146. Ion exchange occurs in the column and the solution containing the metal species then enters channel 152 and passes between electrodes 142 and 144. Detector 140 is provided with a reference electrode 156 located adjacent a solution exit port 160. Conducting electrode 142, counter electrode 144 and reference electrode 156 are coupled to potentiostat 16 via wires 170, 172 and 174 respectively.

Referring to FIG. 4 and FIG. 4A, the structure and fabrication of a detector electrode 50 similar to composite electrode 12 will now be described. Electrode 50 comprises an intimate mixture of a zeolite component 52 and a chemically inert and electrically conductive material 54, see the blowup in FIG. 4A. This mixture can be immobilized on a conductive substrate 56 using a binder component (not shown). Contained within the interior pores of zeolite component 52 are an electroactive species (not shown). Electrical contact is made to electrode 50 with an electrically conducting wire 58.

The criteria for conductive component 54 is that it be chemically inert in the medium of use. The binder component may be chosen from a wide variety of chemically stable and inert polymer binders such as polystyrene, teflon™, various epoxies, KEL-F™ and polythene to mention just a few. As described above, the binder and conductor are separate components which are mixed with the zeolite component to give a composite electrode. Alternatively, the binder and conductor may be in a prefabricated or pre-mixed form, such as epoxy bonded graphite. FIG. 5 illustrates an alternative embodiment of detector electrode 50 wherein the zeolite and conductive component mixture shown at 60 are formed by mixing the zeolite with an epoxy bonded graphite. Note that the binder components previously mentioned could also be used in this embodiment. Also, the manner in which electrical contact is made to the zeolite/binder composite 60 can either be by direct electrical contact or by using a conductive mercury pool, silver epoxy or other metal containing epoxies.

Figure 6:
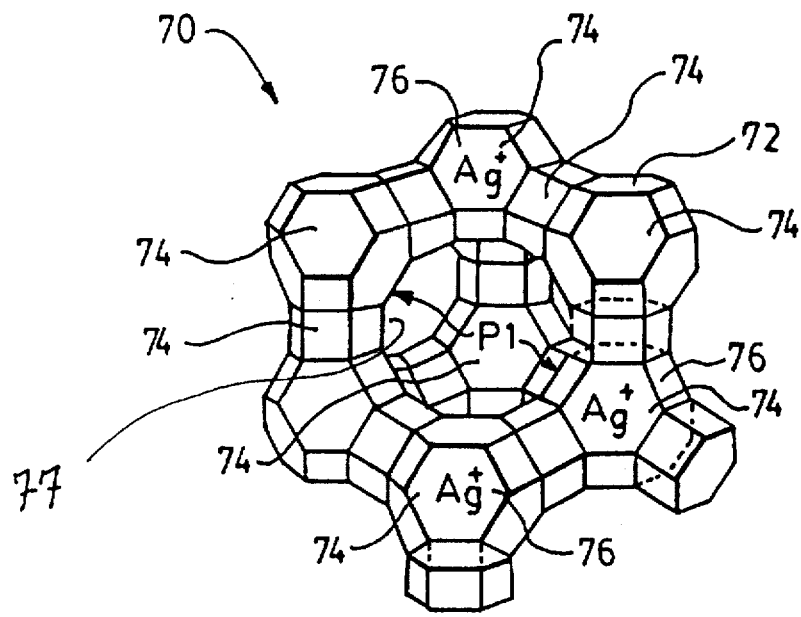
FIG. 6 is a schematic perspective view of the framework structure of zeolite Y.

The principle on which the zeolite based solution phase ion and small molecule detector device of the subject invention works is as follows. The zeolite family of materials are microporous, crystalline solids with an open three dimensional crystal structure having cages or cavities with well known pore diameters. Different species of zeolite have different crystal structures and different sized cages. Referring to FIG. 6, there is shown a zeolite species 70 (usually referred to as zeolite Y) from the zeolite family of materials having a framework 72, small cages 74, and larger supercages 77 with a well defined pore diameter P1. Since the zeolite is an aluminosilicate, framework 72 possesses a negative charge, thus during synthesis a charge balancing counter ion such as $Na^+$ or $K^+$ is incorporated into the cages (not shown).

In the detector of the present invention, an electroactive species 76 (shown as $Ag^+$) is incorporated into cages 74 and 77 of the zeolite either before or after fabrication of the detector electrode using a known technique, e.g. ion-exchange. As will be discussed below, it is not necessary that a complete ion-exchange occurs for the detector to work effectively.

The term "electroactive ion" refers to ions that can be either electrochemically oxidized or reduced in the liquid solution of interest, in other words the reversible potential of the species lies within the stability range of the solution. The electroactive species which is incorporated into the zeolite may be chosen from a large number of metals including but not restricted to silver (Ag), copper (Cu), nickel (Ni), cobalt (Co) and manganese (Mn) to mention just a few. The criteria to be considered in the selection of the electroactive species is that it be easily ion-exchanged into and out of the zeolite and that it be readily reduced or oxidized in the electrolyte of interest.

The term "electroinactive ion" refers to ions that cannot be oxidized or reduced within the stability region of the electrolyte. The zeolite based ion detector can be used to detect ions not normally amenable to direct amperometric detection, e.g. alkali metals since the reversible potentials of these species lie outside the stability region of most aqueous solutions. In this context, electroinactive also refers to metal species which have reduction or oxidation potentials within the stability region of the electrolyte but have high overpotentials on the composite electrode so that they do not undergo electrochemical reaction at any significant rate within the stability region of the electrolyte. In addition, ions other than "electroinactive ions" defined above may be determined. Specifically, ions that are reducible or oxidizable (within the stability region of the electrolyte) but at potentials outside of that of the detector electrode (set by the potentiostat). The DC potential applied to the detector electrode is not cathodic or anodic enough to directly reduce or oxidize the ion of interest. Also, solution phase ions that are oxidized or reduced at the potential of the detector electrode can be determined indirectly using calibration curves.

Referring to FIGS. 1, 2 and 4-6, in operation the species present in solution 20 (hereinafter referred to as the analyte species or analyte ion) can be determined amperometrically when the electroactive species 76 is either reduced (or oxidized) at a site on a conductive portion of composite electrode 12. For this to occur electroactive species 76 must exit zeolite cage 74 and once on the surface of conducting portion 54 of electrode 12 it can be either reduced or oxidized. For electroactive species 76 to leave the zeolite cage it must be replaced by analyte species from solution 20 in order to maintain charge neutrality on zeolite 70. This replacement occurs by ion-exchange. Therefore the analyte species exchanging with the electroactive species must be capable of accessing interior cages via the zeolite pores.

The detector illustrated in FIG. 3 operates on the same principle except that the ion exchange reaction takes place in zeolite column 146 and the liberated electroactive species flows in solution past conducting electrode 142.

The following steps are involved in the method disclosed herein for detecting an analyte ion in aqueous or non-aqueous solution.

i. Solvated analyte cation ion-exchanges with electroactive cation in the zeolite;

ii. electroactive cation exits the zeolite pore and diffuses across electrode surface to a conductive site; and iii. electroactive cation oxidized or reduced depending on the electrode potential. Current flowing due to reduction or oxidation is recorded and used to determine concentration of analyte species.

These reaction steps may be represented in the following way, using $Ag^+$ as the electroactive component and $K^+$ as the analyte species being detected:

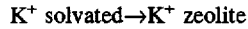
$K^+$ solvated→$K^+$ zeolite

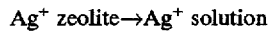
$Ag^+$ zeolite→$Ag^+$ solution

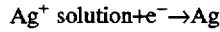
$Ag^+$ solution+$e^-$→$Ag$

Thus while the electrochemical current is due to the reduction (or oxidation) of the electroactive species, the magnitude of this current is controlled by the concentration of the analyte species in solution. That is, by the rate of ion-exchange between electroactive and analyte species.

Since the zeolites have well defined pore sizes, if the solvated cation from the electrolyte is too large to enter the zeolite pores then electroactive species 76 cannot exit the zeolite. Thus no electrochemical reaction will occur and zero Faradaic current will be detected. Since there are a large number of zeolite materials having a broad range of pore diameters, the detector may therefore be designed for size selective detection of the solution phase species. Specifically, size sensitivity may be achieved by utilizing zeolites having a pore size comparable to the size of the solvated ion of interest while excluding larger species.

Note that the detector electrode described herein can also be used to determine one component of a multi-component system providing that the zeolite pore size is matched to the component of interest. An alternative mechanism whereby this can occur where two components can enter the zeolite is through preferential adsorption of one component which has been observed and reported in the open literature.

Figure 7:
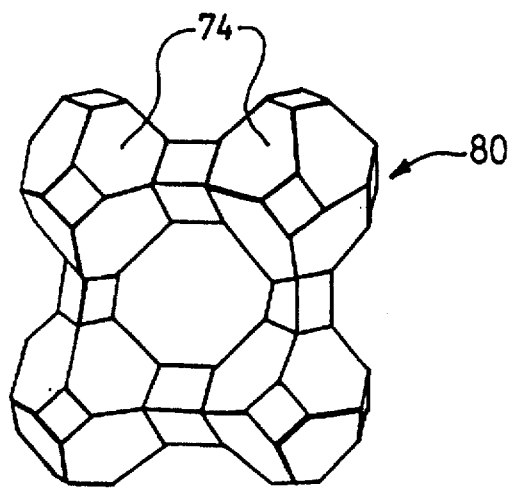
FIG. 7 is a perspective diagrammatic view of the framework structure of zeolite A.
Figure 8:
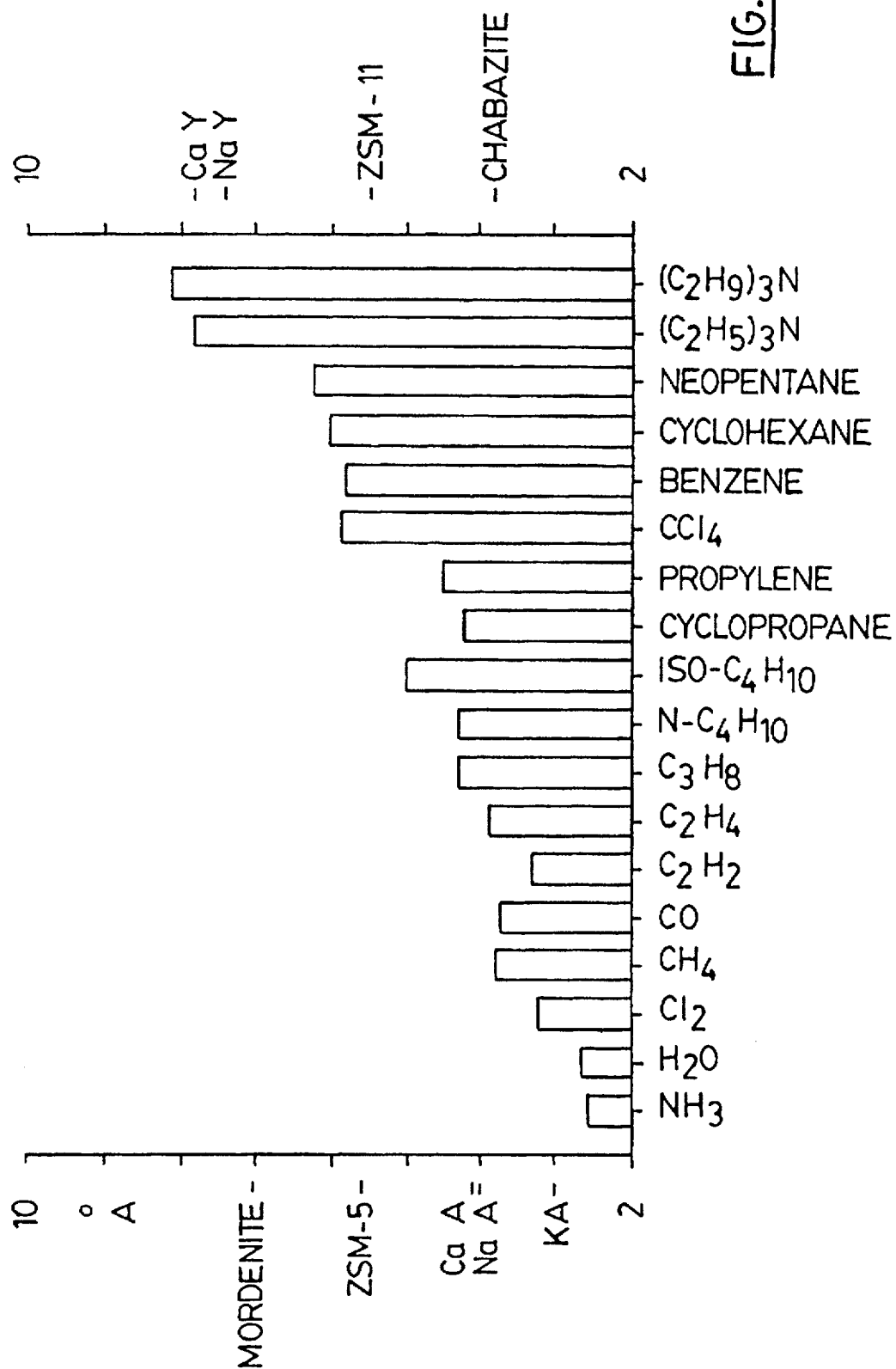
FIG. 8 is a representation of the pore or cage sizes of various zeolite types compared with the kinetic diameters of some common molecules.

FIG. 7 shows another zeolite type, known as zeolite A at 80. Referring to FIG. 8, the pore sizes of various zeolite types are compared with the kinetic diameters of various analyte species.

In the case where the detector electrode is used to quantitatively determine the concentration of BTEX in solution, the operation of the detector depends on the electroactive ion being placed inside the cages 74 in FIG. 6, also referred to as "small channel silver ions" while the electroactive ions are removed from the supercages 77 and replaced by a larger cation which does not ion exchange with the remaining silver ions in the small cages. When placed in a liquid containing small molecules being detected for, the electroactive ions 76 in the small cages 74 exit the zeolite and thus enter the solution by virtue of a strong interaction with the organic molecule which egresses into the supercage 77 from solution. Ion exchange occurs because the ejected electroactive ion is charge balancing. Electroinactive ions in solution replace the silver ions in the small cages to maintain charge balance. The type of interaction envisaged between the electroactive ion and the small molecule is typical of that for bonding between a transition metal and an organic molecule containing Π electrons, and is known as a d Π-p Π interaction. Interactions of this type have been observed for $Ag^+$ and benzene. Also, silver salts are soluble in benzene solution by virtue of the d Π-p Π bond between silver and benzene. For these reasons $Ag^+$ is the preferred electroactive ions in this aspect of the invention.

More specifically, in the case where the zeolite detector electrode is used to detect BTEX in solution, a zeolite having both large and small cages is preferred, such as shown in FIG. 6. When the electroactive moiety 76 is placed in the small cages 74 of the zeolite it can also be prevented from exiting the zeolite into the solution phase by placing a cation, for example $NH_4+$, which is too large to enter the small cages 74 into the supercages 77. Thus, on the timescale of the electrochemical determination, ion exchange between electroactive moiety 76 in the smaller cages and the ammonium ions in the supercages 77 is prevented. The presence of the organic molecule satisfying the size requirements is detected based on the principle that the electroactive species 76 can be forced to leave the zeolite by virtue of a strong interaction with solution phase BTEX, which can also enter the supercages after the silver cations originally present in the larger supercages have been ion exchanged with the electroinactive counter cation during preparation of the zeolite.

The key to the operation of this aspect of the small molecule detector is the presence of both small and large cages in the zeolite. The electroactive ion (preferably $Ag^+$) is then trapped in the small cages. Since the zeolite is an electrical insulator, the $Ag^+$ in this environment is not electrochemically active. Thus in aqueous solution not containing BTEX no faradaic currents due to $Ag^+$ reduction can occur.

In this embodiment of the method for detecting the presence of the organic molecules such as BTEX in solution, the steps may be represented in the following way using $Ag^+$ as the electroactive component and benzene as the analyte species being detected.

(i) Small molecule in solution interacts strongly with electroactive moiety in the zeolite small cages/channels. This can occur directly from solution following the ingress of the molecule into the zeolite via the large channels or supercages 77.

(ii) The silver cations 76 exit the small channels or cages 74 and thereafter exit the zeolite by ion exchange with electroinactive cations in the solution phase.

(iii) Silver cations 76 reach the conductive part of the electrode and there undergo a reduction (or oxidation depending on the potential) by virtue of the potential bias applied to the electrode.

(iv) Current caused by reduction (or oxidation) is recorded. The magnitude of this current or that caused by subsequent re-reduction or oxidation is used to monitor the concentration of BTEX (or the small molecule analyte) in solution.

These steps be represented in the following way, noting that in the example the counter ion is ammonium and the electroactive ion in the zeolite is the silver cation 76.

1) zeolite electrode preparation: removal of $Ag^+$ from zeolite supercages zeolite (with Ag+ in small cages and supercages) $+NH_4^+$ (solution)$\rightarrow NH_4^+$ (in the supercages)$+Ag^+$ (zeolite small cages)

2) BTEX measurement: zeolite ($NH_4^+$ in supercages, $Ag^+$ in small cages)+BTEX$\rightarrow AG^+$ (solution) $Ag^+$ (solution)+e- $\rightarrow$Ag (reduction at electrode)

The suppression of any current due to the absence in solution of a small electrolyte ion (that is not size excluded from the zeolite) is of great importance. This is an attractive feature of the detector since the mobile phase used in ion chromatography is an electrolyte solution. Any current flowing due to this ion which is at a very high concentration could swamp the response of the detector. Thus the detector circumvents the dynamic range problems described earlier.

The size selectivity of the detector electrode of the present invention may be considered to form the basis of a size selective background current suppression technique whereby small concentrations of analyte ions may be readily detected in a sea of background size excluded electroinactive and electrolyte ions.

The presence of electroactive impurity cations in the solution of interest having reversible potentials within the stability range of the electrolyte in addition to good kinetics for oxidation or reduction may also lead to swamping of the detector if they are present at high enough concentration. This is because direct oxidation or reduction of the impurity species on the conductive portion of the electrode may be possible with current magnitudes greater than those achievable by reaction of the electroactive species from the zeolite. One way to avoid this potential problem is to incorporate a "poison" into the composite electrode which serves to increase the overpotential of the redox reactions of any "impurity" species present. It will be appreciated that this poison preferably has no significant effect on the kinetics of the redox reactions of the electroactive species. Another way of overcoming this potential problem may be to change to an electroactive ion which allows the use of a DC potential where the impurity ions cannot be reduced or oxidized.

In addition to being a size sensitive ion detector, the detector may also be used to detect trace amounts of water in non-aqueous solvents such as organic feedstock. In an organic solution containing cation species such as $K^+$ or $Na^+$, with no water present the cations will be solvated with organic molecules of the solvent. The size of this solvation sheath will vary depending on the size and dipole moment of the organic molecules. However, if a small amount of water is present then cations may be hydrated with water molecules if the latter have a dipole moment greater than the organic molecules. Generally, a water hydrated cation will be much smaller than the same cation having a solvation sheath comprised of organic molecules. By appropriate choice of the zeolite channel or cage size, an organically solvated cation can be size excluded from the zeolite while the same hydrated cation can gain access to the zeolite cage whereby the cation can ion-exchange with the electroactive species with the result that an electrochemical current will be observed. In addition zeolite A (FIG. 7) is a hydrophilic material and is therefore a useful material for water detection.

It will be appreciated that the detector disclosed herein may be used for detecting other small molecules such as for example propanol and methanol to mention just a few.

Referring to FIG. 9, another embodiment of the ion and small molecule detector is shown at 100 provided with a detector electrode 102 comprising a zeolite component 104 in the form of a plug or thin membrane and a separate conducting electrode component 106. Zeolite component 104 is provided with an electroactive species (not shown) and an optional binder component which acts to hold the zeolite powder together. Electrode 106 is used to amperometrically detect liberated electroactive species. Detector 100 operates on the same principle as detector 10 and the same reaction sequence is followed as described previously but with the exception that instead of liberated species diffusing to a site on zeolite portion 104, it now diffuses to conductive electrode 106 where it is reduced or oxidized and thereby amperometrically detected. Conductive electrode 106 may be fabricated from a wide variety of materials including but not restricted to Pt, Au, Hg, Ag and carbon. Detector 100 may be the preferable configuration when direct electrical contact between zeolite portion 104 and the rest of the detector 100 is not feasible. For example, composite electrode 12 of FIG. 2 is replaced by a conducting electrode while a separate zeolite portion, in the form of a plug or thin membrane, is attached to solution inlet 34.

In another alternative embodiment of the electrochemical based ion and water detector of the subject invention, the electrically conducting component, graphite powder in the examples above, may be replaced by other suitable materials. Thus while carbon is preferable for many aqueous applications and non-aqueous applications, in very strong acids or bases it may be preferable to use the more chemically resistant conductive suboxide of titanium known as Ebonix*, which has the same conductivity as graphite. Other oxide based conductors may also be employed.

In still another embodiment, the insulating zeolite may be confined within a microporous, stable and electrically conducting polymer matrix. In addition to providing the desirable electrical conductivity, this polymer may also serve the role of the binder component thereby eliminating this separate component.

While the electrochemical based ion and small molecule detector of the present invention preferably uses zeolites as the active ion-exchange component, those skilled in the art will recognize that other ion-exchange materials may be used with pores having an appropriate size distribution relative to the species the system is designed to detect. For example the materials used in ion-exchange columns may be encapsulated into an electrode arrangement by mixing with a suitable conducting component and using a suitable binder to immobilize the mixture on an electrode. Since both positively and negatively charged ion-exchange materials are readily available, both cation and anion electrochemical detectors could be fabricated based on these ion-exchange materials.

Numerous experimental studies confirming the efficacy of the detector of the present invention for detecting ions and water have been carried out. The results of three of these studies will now be presented. It will be appreciated that the detection regimes used as examples here do not reflect the ultimate detection limits achievable for the detector electrode.

EXAMPLES

1. Ion Detector

The zeolite detector used in both modes (ion and water sensor) used silver as the electroactive species. The $Ag^+$ containing detector electrode was prepared by ion exchanging about 1 gram of zeolite Y (ion detector) zeolite A (water detector) using a solution of 0.01M silver nitrate. Following an overnight exchange, the zeolite sample was carefully washed, air dried, lightly ground to a fine powder and stored over saturated ammonium chloride solution.

The procedure used to fabricate the electrodes comprised lightly grinding about 100 mg of the ion exchanged zeolite. This was then dispersed in a solution of tetrahydrofuran (THF) containing 10 mg of polystyrene and then vigorously stirred. Using a micro-pipette, 20 microliter aliquots of this solution were then applied to conductive indium tin oxide (ITO) coated glass blanks (Donnely-Meirs Corp., Michigan) which served as the conducting substrate of the working electrode. The electrode was then air dried. The weight of the electrode coating was typically about 1.5 mg.

Figure 10:
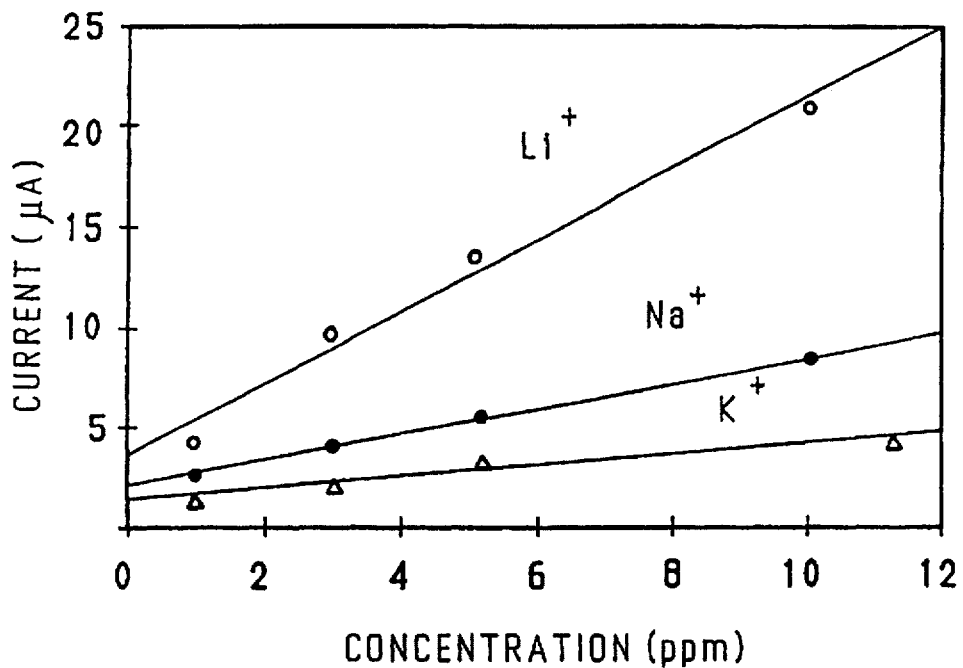
FIG. 10 illustrates experimental data recorded using the detector electrode as an ion detector for the detection of $K^+$, $Na^+$ and $Li^+$ in 0.10M tetrabutylammonium perchlorate in methanol/$H_2O$ with silver as the electroactive species.

A solution of 0.10M tetrabutylammonium perchlorate in methanol/$H_2O$ was prepared. The detector electrode was then tested by standard addition of various cations as shown in FIG. 10. These data clearly shown the efficacy of the detector for detecting ionic species in solution.

2. Water Detector

Figure 11:
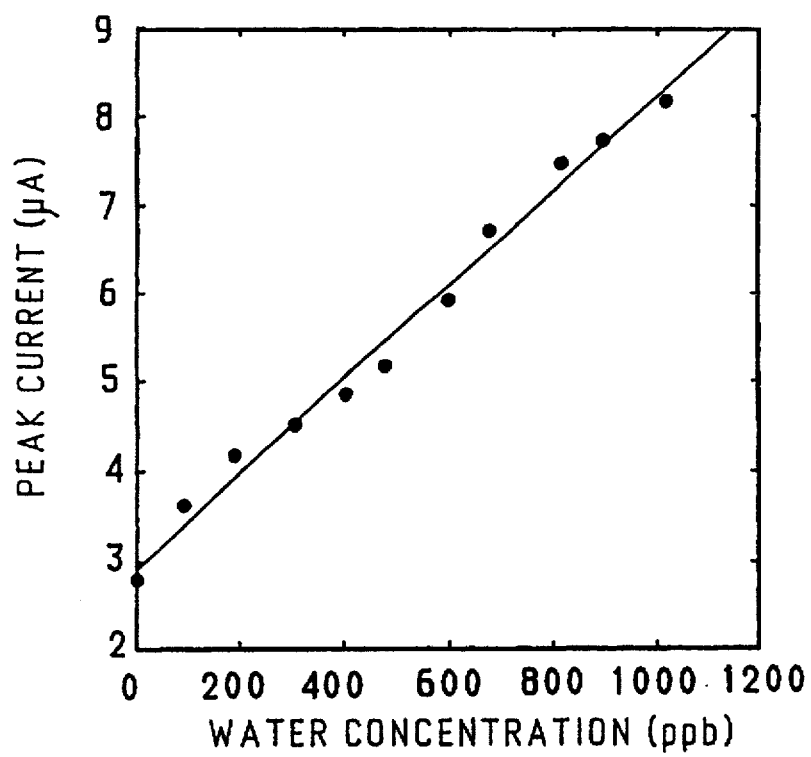
FIG. 11 shows a calibration curve constructed using data obtained in a standard addition experiment in an electrolyte of 0.1M LiClO$_4$ in dry n,n-dimethylformamide.

The zeolite detector electrode containing silver was fabricated in essentially the same manner as described above. A solution of 0.10M lithium perchlorate in n,n-dimethyl formamide was prepared. The solvent glassware etc. and supporting electrolyte were thoroughly dried before use. All experimentation was performed in a Vacuum Atmospheres dri-box. FIG. 11 illustrates the response of the detector electrode to trace concentrations of water in a standard addition experiment. These data clearly show the efficacy of the detector for detecting water in organic liquids, between 100 and 1,000 ppb.

Figure 12:
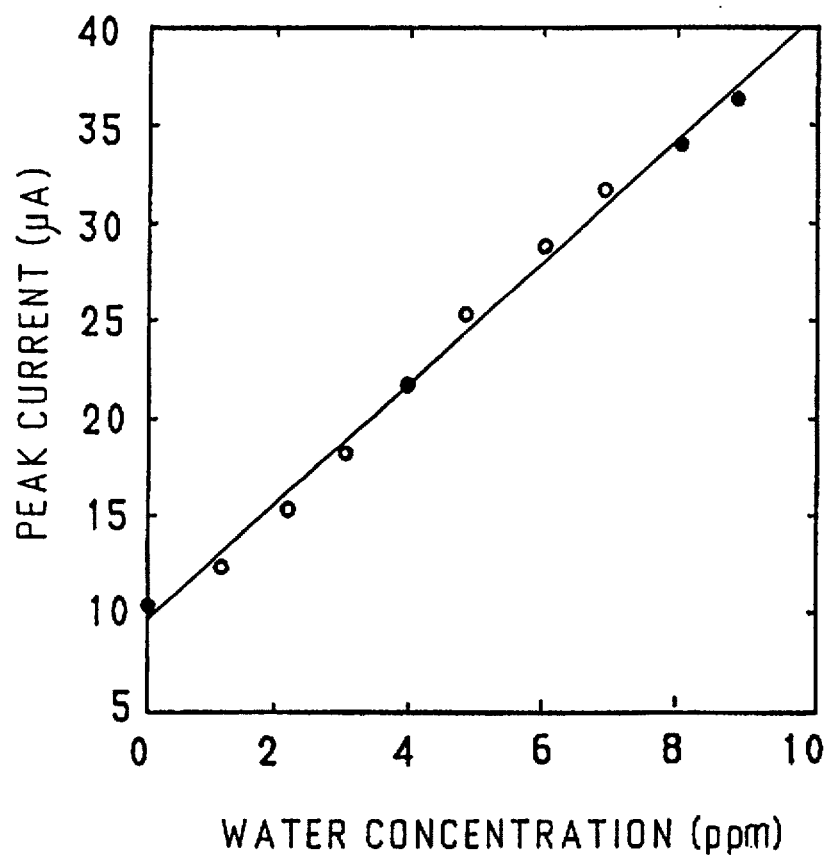
FIG. 12 shows a calibration curve constructed using data obtained in a standard addition experiment in an electrolyte of 0.1M LiClO$_4$ in dry n,n-dimethylformamide.

With reference to FIG. 12 it is also shown that in the same solvent water can be detected from 1–9 ppm. This is also the result of a standard addition experiment.

Note that these data are the result of anodic stripping experiments. In these experiments the electrode was held at a potential negative of the reversible potential of silver for a period Of time during which silver was ion exchanged and plated onto the conducting portion of the detector electrode. After a certain period of time the detector electrode potential was scanned positively and the plated silver stripped. Referring to FIGS. 10–12, it is evident the detector will operate in the sub ppm range for both water and cations.

3. Small Molecule and BTEX Detection

The zeolite detector electrode containing silver was fabricated in a different manner to that described above. First the parent NaY zeolite (FIG. 6) was ion exchanged in 0.1M $AgNO_3$ aqueous solutions until 100% of the cation exchange capacity was reached. The sample was then analysed to have 56 silver ions per unit cell of the zeolite. This material was then exposed to aqueous solutions of $NH_4SCN$ is order to ion exchange the silver ions out of the large supercages 77 of the zeolite (see FIG. 6). The procedure used to fabricate the detector electrode were exactly the same as those described in example 1 above. The electrodes thus formed were then used in the electrochemical determinations of BTEX in water. In this section the detection of benzene in water is used as an example.

Figure 13:
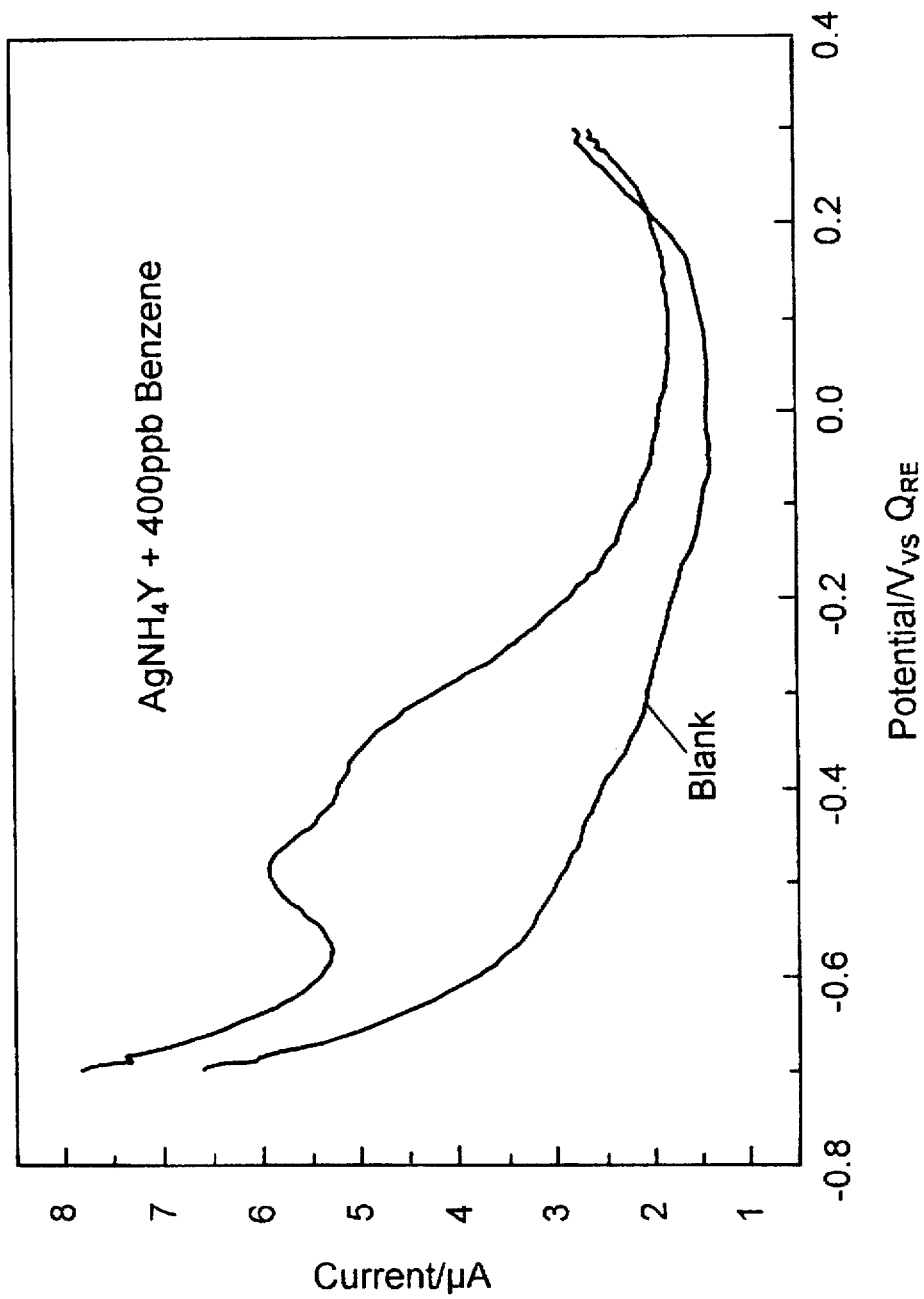
FIG. 13 shows experimental data using the detector electrode as a molecule detector for benzene at 400 ppb in water with a 0.1M ammonium nitrate electrolyte at a scan rate of 20 mV/s and potentials referenced to a Pt wire quasi-reference electrode (QRE).

The procedure used in order to show that detection was possible was as follows. The electrolyte solution was prepared using a 0.1M $NH_4NO_3$ solution in water. Note here that the counter ion in solution must also be too large to enter the zeolite small channel system on the timescale of the electrochemical experiment. In the case the ammonium ion is used. Other ions such as $Ba^{2+}$ and $Sr^{2+}$ could be used. The solution was then thoroughly purged with dry nitrogen gas in order to drive out dissolved oxygen. After this procedure the electrode was immersed in solution as the voltage on the electrode is maintained at a value negative of the standard reduction potential for silver for thirty seconds. Then an anodic bias was applied to the electrode in the fashion of a differential pulse anodic stripping experiment. This is the blank or background scan shown in FIG. 13. The small molecule at a known concentration was admitted to the test solution which is stirred vigorously until the anodic scan was performed. In this case the benzene in solution forces silver to exit the zeolite and enter the external solution where it can be reduced at the negatively charged electrode. The anodic scan then applied strips off the electroplated silver giving rise to a current that is proportional to the concentration of benzene in solution. A typical result of this type of experiment in which the benzene concentration is about 400 ppb is shown in FIG. 13.

There are numerous techniques available to increase the detection limit of the ion and water and small molecule detection method forming the present invention. Those skilled in the art will appreciate that various AC techniques as well as pulsed voltammetry are available for improving the detection limit of DC voltammetry through the suppression of charging currents. In addition, the fact that the anodic waves for the water sensor discussed above are stripping peaks means that this sensor can operate in a manner similar to stripping analysis in polarography. This is the most sensitive electroanalytical technique so far developed and detection limits for many analytes less than 0.01 ppb are routine.

While the method of detecting electroinactive ions and small molecules forming the subject invention has been described and illustrated with respect to the preferred embodiments, it will be appreciated by those skilled in the art that numerous variations of these embodiments may be made without departing from the scope of the invention disclosed herein.

Therefore what is claimed is:

1. A method for detecting small molecules such as benzene, toluene, ethylbenzene or xylene in aqueous liquid samples, comprising the steps of:

a) providing a zeolite having a plurality of first cages and a plurality of second cages larger than said first cages, said small molecules being able to access said zeolite on the basis of size, said first cages containing electroactive ions therein, said second cages containing electroinactive counter cations therein;

b) providing an aqueous liquid sample to be tested for small molecules and contacting said aqueous liquid sample with said zeolite, whereby when small molecules are present at least some of said electroactive ions in said first cages are released into the liquid sample by small molecules entering said second cages and wherein said small molecules couple with corresponding electroactive ions in the first cages and exit said zeolite into the liquid sample; and c) bringing the liquid sample containing the electroactive ions into contact with an electrode after the liquid sample has contacted said zeolite, applying a potential to the electrode with respect to a counter electrode effective to cause an electrochemical reaction of the electroactive ions.

2. The method according to claim 1 including recording an electrical current resulting from the electrochemical reaction and relating said current to a concentration of said small molecules in said liquid.

3. The method according to claim 2 wherein said aqueous liquid sample is flowed through a flow system containing the zeolite, electrode and counter electrode, the aqueous liquid sample first being flowed into contact with the zeolite and then into contact with the electrode.

4. The method according to claim 3 wherein the zeolite is zeolite Y.

5. The method according to claim 4 wherein said electroactive ions are $Ag^+$.

6. The method according to claim 5 wherein said electroinactive counter cation is $NH_4+$.

7. A method for detecting small molecules such as benzene, toluene, ethylbenzene or xylene in aqueous liquid samples, comprising the steps of:

a) providing a zeolite having a plurality of first cages and second cages, the second cages having a larger volume than the first cages, said small molecules being able to access said zeolite on the basis of size, said first cages containing electroactive ions therein and said second cages containing electroinactive counter cations therein;

b) flowing an aqueous liquid sample to be tested for small molecules into contact with said zeolite, whereby at least some of said electroactive ions in the first cages are released into the aqueous liquid sample by small molecules entering said second cages wherein said small molecules couple with corresponding electroactive ions located in the first cages and exit said zeolite; and thereafter c) flowing the liquid sample into contact with an electrode downstream of said zeolite, applying a potential to the electrode with respect to a counter electrode effective to cause an electrochemical reaction of the electroactive ions.

8. The method according to claim 7 including recording an electrical current resulting from the electrochemical reaction and relating said current to a concentration of organic molecules in said liquid.

9. The method according to claim 8 wherein said electroactive ions $Ag^+$.

10. The method according to claim 9 wherein the zeolite is zeolite Y.

11. The method according to claim 10 wherein said electroinactive counter cation is $NH_4^+$.

* * * * *